(12) United States Patent
Koehler (10) Patent No.: US 12,023,490 B2
(45) Date of Patent: Jul. 2, 2024

(54) DEVICE, SYSTEM AND METHOD FOR KILLING VIRUSES IN BLOOD THROUGH ELECTRODE WIRES

(71) Applicant: Tim Koehler, Weaverville, NC (US)

(72) Inventor: Tim Koehler, Weaverville, NC (US)

(73) Assignee: Rain Scientific, Inc., Cornelius, NC (US)

( * ) Notice: Subject to any disclaimer, the term of this patent is extended or adjusted under 35 U.S.C. 154(b) by 1275 days.

(21) Appl. No.: 16/411,432

(22) Filed: May 14, 2019

(65) Prior Publication Data
US 2020/0009375 A1  Jan. 9, 2020

Related U.S. Application Data (60) Provisional application No. 62/671,589, filed on May 15, 2018.

(51) Int. Cl.
*A61N 1/30* (2006.01)
*A61N 1/04* (2006.01)
(Continued)

(52) U.S. Cl.
CPC .......... *A61N 1/306* (2013.01); *A61N 1/0428* (2013.01); *A61N 1/05* (2013.01); *A61K 33/242* (2019.01);
(Continued)

(58) Field of Classification Search
CPC ...... A61K 33/242; A61K 33/34; A61K 33/38; A61M 1/14; A61M 1/3607; A61M 1/3687;
(Continued)

(56) References Cited

U.S. PATENT DOCUMENTS 4,292,968 A    10/1981  Ellis
5,401,239 A *   3/1995  Stephen ................... A61N 1/30
                                                    604/20
(Continued)

FOREIGN PATENT DOCUMENTS

CN    105251034 A    1/2016
CN    106215302 A    12/2016
(Continued)

OTHER PUBLICATIONS

Kim TN, Feng QL, Kim JO, et al. Antimicrobial effects of metal ions (Ag+, Cu2+, Zn2+) in hydroxyapatite. J Mater Sci Mater Med. 1998; 9(3):129-134.
(Continued)

*Primary Examiner* — Shefali D Patel
(74) *Attorney, Agent, or Firm* — Venable LLP (57) ABSTRACT

A device for killing blood-borne pathogens, and a method of using the device to effectively remove the blood-borne pathogens from a body of a human or an animal is claimed. The device comprises a wire that is inserted into a bloodstream of a patient, which releases metallic ions which effectively kill the pathogens. There are several embodiments, each of which has a combination of covered and uncovered portions of the wire. The wire is electrically connected to both a source of power and a power supply with a printed circuit board or a controller/software, which controls an intensity and a duration of a treatment.

33 Claims, 7 Drawing Sheets

(51) Int. Cl.
*A61N 1/05* (2006.01)
*A61K 33/242* (2019.01)
*A61K 33/34* (2006.01)
*A61K 33/38* (2006.01)
*A61M 1/14* (2006.01)
*A61M 1/36* (2006.01)
*A61M 25/00* (2006.01)

(52) U.S. Cl.
CPC .............. *A61K 33/34* (2013.01); *A61K 33/38* (2013.01); *A61M 1/14* (2013.01); *A61M 1/3607* (2014.02); *A61M 25/0012* (2013.01); *A61M 2202/20* (2013.01); *A61M 2202/206* (2013.01)

(58) Field of Classification Search
CPC .. A61M 2025/0056; A61M 2202/0413; A61M 2202/20; A61M 2202/203; A61M 2202/206; A61M 2205/0233; A61M 2210/12; A61M 25/0012; A61M 37/00; A61N 1/04; A61N 1/0428; A61N 1/05; A61N 1/30; A61N 1/303; A61N 1/306; A61N 1/325
See application file for complete search history.

(56) References Cited

U.S. PATENT DOCUMENTS

| | | | |
|---|---|---|---|
| 6,066,489 A * | 5/2000 | Fields | A61B 18/1492 435/236 |
| 6,495,367 B1 | 12/2002 | Isogawa et al. | |
| 6,539,252 B1 | 3/2003 | Fields et al. | |
| 7,460,914 B2 * | 12/2008 | Mandrusov | A61N 1/0568 604/20 |
| 7,807,112 B2 | 10/2010 | Denes et al. | |
| 8,057,680 B2 | 11/2011 | Degim et al. | |
| 8,349,604 B2 | 1/2013 | Mohapatra et al. | |
| 9,199,026 B2 | 12/2015 | Greenberg et al. | |
| 9,320,832 B2 | 4/2016 | Joseph et al. | |
| 9,375,525 B2 | 6/2016 | Greenberg et al. | |
| 9,849,282 B2 | 12/2017 | Fuller et al. | |
| 2002/0183684 A1 * | 12/2002 | Dev | A61N 1/325 977/932 |
| 2003/0208192 A1 | 11/2003 | Truckai et al. | |
| 2006/0147533 A1 | 7/2006 | Balasubramanian et al. | |
| 2008/0085301 A1 | 4/2008 | Lane | |
| 2008/0195033 A1 | 8/2008 | Eagleson et al. | |
| 2008/0269665 A1 | 10/2008 | Petersen | |
| 2010/0113871 A1 | 5/2010 | Dias et al. | |
| 2010/0125238 A1 * | 5/2010 | Lye | A61N 1/306 604/21 |
| 2015/0017258 A1 | 1/2015 | Azzazy et al. | |
| 2015/0030651 A1 | 1/2015 | Minturn | |
| 2015/0083596 A1 * | 3/2015 | Hester | A61M 39/16 204/600 |
| 2015/0320998 A1 * | 11/2015 | Hester | A61M 25/01 604/501 |
| 2015/0320999 A1 | 11/2015 | Nuccitelli et al. | |
| 2016/0074791 A1 | 3/2016 | McClung, III | |
| 2016/0287741 A1 | 10/2016 | Harris et al. | |

FOREIGN PATENT DOCUMENTS

| | | | | |
|---|---|---|---|---|
| GB | 2189677 | A | 11/1987 | |
| JP | H11322619 | A | 11/1999 | |
| JP | 2004041711 | A | 2/2004 | |
| KR | 200425112 | Y1 | 8/2006 | |
| KR | 200425423 | Y1 * | 9/2006 | .............. A61N 1/30 |
| KR | 20060123823 | A | 12/2006 | |
| KR | 20150117376 | A | 10/2015 | |

OTHER PUBLICATIONS

Lemire JA, Harrison JJ, Turner RJ. Antimicrobial activity of metals: mechanisms, molecular targets and applications. Nat Rev Microbiol. 2013;11(6):371-384.

Lansdown AB. A pharmacological and toxicological profile of silver as an antimicrobial agent in medical devices. Adv Pharmacol Sci. 2010; vol. 2010, 16 pages.

Berger TJ, Spadaro JA, Bierman R, Chapin SE, Becker RO. Antifungal properties of electrically generated metallic ions. Antimicrob Agents Chemother. 1976; 10(5):856-860.

Berger TJ, Spadaro JA, Chapin SE, Becker RO. Electrically generated silver ions: quantitative effects on bacterial and mammalian cells. Antimicrob Agents Chemother. 1976; 9(2):357-358.

Jung W, Koo H, Kim K, Shin S, Kim S, Park Y. Antibacterial activity and mechanism of action of the silver ion in *Staphylococcus aureus* and *Escherichia coli*. Appl Environ Microbiol. 2008; 74(7):2171-2178.

Hall RE, Bender G, Marquis RE. In vitro effects of low intensity direct current generated silver on eukaryotic cells. J Oral Maxillofac Surg. 1988; 46(2):128-133.

Thibodeau EA, Handelman SL, Marquis RE. Inhibition and killing of oral bacteria by silver ions generated with low intensity direct current. J Dent Res. 1978; 57(9-10):922-926.

Spadaro JA, Berger TJ, Barranco SD, Chapin SE, Becker RO. Antibacterial effects of silver electrodes with weak direct current. Antimicrob Agents Chemother. 1974;6(5):637-642.

Ojha A, Nandi D, Batra H, et al. Platelet activation determines the severity of thrombocytopenia in dengue infection. Sci Rep. 2017; 7:41697.

Holt KB, Bard AJ. Interaction of silver(I) ions with the respiratory chain of *Escherichia coli*: an electrochemical and scanning electrochemical microscopy study of the antimicrobial mechanism of micromolar Ag+. Biochemistry. 2005; 44(39):13214-13223.

Abdulkareem et al., Silver and its application as an antimicrobial agent. Expert Opinion on Therapeutic Patents. 2005; 15(2):125-130.

Santo CE, Quaranta D, Grass G. Antimicrobial metallic copper surfaces kill *Staphylococcus haemolyticus* via membrane damage. MicrobiologyOpen. 2012; 1(1):46-52.

Sisson TR, Whalen LE, Telek A. The blood vol. of infants. II. The premature infant during the first year of life. J Pediatr. 1959; 55:430-446.

Edwards-Jones V. The benefits of silver in hygiene, personal care and healthcare. Letters in Appl Microbiol. 2009; 49(2):147-152.

M.R. Pingle et al., Multiplexed Identification of Blood-Borne Bacterial Pathogens by Use of a Novel 16S rRNA Gene PCR-Ligase Detection Reaction-Capillary Electrophoresis Assay, J. Clin. Microbiol. 45, No. 6: 1927-1935 (2007).

Aug. 14, 2022 International Search Report and Written Opinion in International Patent Appln. No. PCT/US2022/024434.

Hashemian et al. A Review on Remdesivir: A Possible Promising Agent for the Treatment of COVID-19, Drug Design, Development and Therapy; 14: 3215-3222, 2020 <URL : https://www.ncbi.nlm.nih.gov/pmc/articles/PMC7425093/>.

* cited by examiner

DEVICE, SYSTEM AND METHOD FOR KILLING VIRUSES IN BLOOD THROUGH ELECTRODE WIRES

CROSS REFERENCE TO RELATED APPLICATIONS

This application claims priority to U.S. Provisional No. 62/671,589, entitled "Device, system and method for killing viruses in blood through electrode wires", filed on May 15, 2018, the contents of which are incorporated by reference.

STATEMENT REGARDING FEDERALLY SPONSORED RESEARCH OR DEVELOPMENT

This invention was not federally sponsored.

BACKGROUND OF THE INVENTION

Field of the Invention

This invention relates to the general field of medical devices and methods, and more specifically toward a device, system and method for killing pathogens in blood. An iontophoretic insert destroys blood-borne pathogens using metallic ions resulting from a silver, gold, copper or other type of metallic wire. As opposed to the prior art, where blood from the arm of the patient is routed to a holding bladder, this invention allows for the insertion of a device into the arm of a patient with the result of killing undesirable pathogens without the need for complex treatment methods involving the removal of blood from a patient during the treatment. There is also prior art on a device that alleges to destroy blood-borne pathogens by inserting an electrode into the patient's body, but this method is quite complex and the necessary machinery to make it work is unwieldy. This provisional application covers several approaches to inserting a device into a vein or artery of the patient, where the devices contain specific metallic nanowires that treat the blood and destroy the blood-borne pathogens both as they flow through the vein or artery around the wire and by ensuring that the proper concentration of ions are delivered to reach and destroy the pathogens.

SHORT SUMMARY OF IMPROVEMENTS OVER THE PRIOR ART

Insulated wire
Volume of Ions released for therapy
Current used to release ions for efficacious therapy
Current and waveform manipulation for most efficacious ionic release for therapy
Skived wire to expose part of wire but with end cap to protect wire from breaking loose.
Spiral wire built into the catheter for dual administration of medicant, including metallic ions
Mesh design built into the catheter for dual administration of medicant, including metallic ions
Spiral or mesh design catheters
Side port catheter for dual administration of medicant, including metallic ions Pathogenic infections of the blood can have a devastating impact on a patient once the pathogen has infected its host. In many cases it ends with the death of the host. The deadlier forms of the blood pathogens are HIV/AIDS and Hepatitis C, Hepatitis A, Hepatitis B, MRSA/Antibiotic resistant bacteria, Vector Borne Diseases—particularly Dengue Virus. HIV can mutate quickly and therefore can be very difficult to create an effective vaccine or drug cocktail that works against it. With Hepatitis C, there are many different strains of the virus and therefore drug therapies that are available can be non-effective and/or have debilitating side effects. The patients that the drugs do not work on are classified as non-responders and their chances for survival are very bleak. One particular strain of Hepatitis C has been linked to a new form of liver cancer that has not been seen before. There has also been a rise in Hepatitis C worldwide due to the popularity of tattooing and the lack of proper hygiene associated with it. The most effective, as supported by authoritative scientific medically published research, way to destroy these blood-borne pathogens is with the use of metallic ions.

Iontophoresis is a physical process wherein ions are driven by an electrical field and flow diffusively through a medium. The prior art has used silver iontophoresis by inserting a catheter into the subclavian vein or the superior vena cava and then placing a silver probe through it and directly into the blood stream. A small electrical current is then applied to the wire in the prescribed amount to release the proper amount of silver nanoparticles, which have a slightly positive charge, to bond to viruses, which has a slightly negative charge. This process destroys the virus by disrupting the functions of the membrane of the virus and thus its ability to survive. This procedure has various challenges associated with it due to its close proximity to the heart, its duration of time needed to be successful and its chances of creating a secondary infection at the entry site.

The prior art also provides devices and methods by which blood is removed from the patient's body, re-routed through a device that uses silver ionized nanoparticles to kill viruses, and the blood is then re-inserted into the patient's body. This method, however, is dependent upon large machines and the ability of a patient to remain "hooked up" to a machine for a long enough period of time such that an improvement in his/her viral counts has been achieved.

The prior art also discloses a method and apparatus for destroying blood borne pathogens is disclosed which utilizes a low intensity direct current to generate positive particles from various metals which destroy viral pathogens. A first electrode comprised of a metal such as silver is inserted into a patient's venous system. Then, a second electrode is placed on the patient's exterior in the vicinity of the first electrode. A low intensity direct current is applied to the first metal electrode which releases silver cations to be bonded to the virus, resulting in the denaturing of the virus. The first electrode is placed in the venous system of the infected patient via a catheter. However, this method relies upon using two separate electrodes where one is inserted into the patient's body and the other upon his or her skin, and, depending on the patient, may require an electrode to be inserted into the patient's jugular vein.

Thus, there has existed a long-felt need for a device and method that efficiently and safely kills pathogens in blood without the need to remove the blood from the patient to achieve the desired result with a minimally invasive technique.

SUMMARY OF THE INVENTION

The current invention provides just such a solution by having a device, system and method for killing pathogens in blood. An iontophoretic wire is inserted via a catheter into a vein or artery of the patient. The wire is made from silver, gold, copper or some combination thereof or any other bio-compatible or bio-medical compatible metal that releases ions. For the wires made from a mixture of metals, the percentage of each can depend upon the result desired. Very specifically for the mixture wires the major metal must be equal or greater than 70% for the target pathogen, anything less of the major metal will not achieve the desired results, i.e. 1) >70% gold, <30 silver 2) >70% Silver, <30% copper 3) >70% gold, <30% silver and copper 4) >70% silver, <30% copper and gold. While the above ranges of metals are used for purposes of illustration, a much wider variety of metal combinations are contemplated and considered part of this patent application. In any case, the goal is to destroy blood-borne pathogens using ions from silver, gold or copper wires that have been inserted into the blood stream of a patient. Appropriate concentrations and durations of metallic ions in blood can kill pathogens without affecting eukaryotic cells, such as erythrocytes (red blood cells) and leukocytes (white blood cells).

Among the other combinations of various metals include: where the metal is equal to or greater than 70% silver and equal to or less than 30% one or more combinations of the other two materials, where the metal is at least 70% gold and equal to or less than 30% one or more combinations of the other two materials, where the electrode is greater than or equal to 70% Copper, and equal to or less than 30% one or more combinations of the other two materials, where the electrode has between 1% and 99% each of gold, silver and copper.

This process will greatly reduce the exposure to life threatening complications as well as a substantial reduction in duration of time needed for the treatment. The procedure could be performed at a doctor's office, at home, at the hospital, the battlefield or as a vacation extended treatment.

The system is fairly basic and simple in both its construction and use. A wire, either manufactured as part of a catheter or manufactured with an insulating cover is Inserted into the patient's blood flow for the treatment of blood-borne pathogens, the determination of which design depends on the pathogen, patient and duration of therapy (or treatment). The duration and intensity of the release of ions is controlled by a proprietary control system or other suitable controlling unit such as a proprietarily designed power supply that we call NANDI, has within it a PCB (printed circuit board) with proprietary software that controls current, waveforms and output for the various programs for treating blood borne pathogens, with a software program that resides outside of the patient's body. The actual design of the wire and the insulation can vary significantly depending on the purpose for which it is manufactured. The actual embodiments and theft function will be described more fully in the Detailed Description section of this application.

It is an object of the invention to provide a device for killing pathogens in blood.

It is another object of the invention to provide a method for killing pathogens in blood.

It is a further object of this invention to provide a device and method for treating blood internally, within the body.

Other objects of the invention include:

The electrode device for the treatment of blood-borne pathogens.

The release of 2 billion to 7 trillion ions per second for the treatment of blood-borne pathogens The output current of 1.25-6.0 microamps to generate an ionic release from our electrode for treatment of blood borne pathogens The length of exposed metallic wire from the distal end of the fully exposed wire design to range from 0.1"-1.0".

The skived wire design which protects the wire from breakage and is safer.

The range of exposed surface area of the metallic wire for the proper release of ions to range from 0.0005 square inches to 0.70 square inches Two new devices for the treatment of antibiotic resistant bacteria and other pathogens, both combination devices which avow the intra-venous release of metallic ions AND the administration of an IV antibiotic medication of other IV therapy. FIRST ONE: two styles, one with interior and the second with an exterior spiral wound metallic wire incorporated into a catheter for ionic release and avows IV drip or other added medicant. Second One: same catheter but with braided wire either on interior or exterior surface of the catheter.

New device, catheter with side port and internal O-ring so that RAIN electrode can be passed into or through catheter and O-ring creates seal, ID of catheter is greater than OD of RAIN Electrode so that IV antibiotic or a medicant can be inserted via side port to allow intravenous application of second therapy The metallurgy of the wire we use to be: 1) 100% copper, silver or gold; 2) > or equal to 70% copper and the remaining 30% silver, gold or a combination of silver and gold; 3) > or equal to 70% silver and the remaining 30% copper, gold or a combination of copper and gold; > or equal to 70% gold and the remaining 30% silver, copper or a combination of silver and copper, 70% copper and the remaining 30% being gold, silver, or some combination of gold and silver, and equal to or greater than 70% copper and the remaining 30% either silver or gold, or some combination of silver and gold.

Placement of the electrode into the venous system of at least 0.5" or greater.

Proprietary current and waveform combinations from our control unit that elicit increased blood flow to the therapy point (where ions are being released) to enhance distribution of ions and minimize biocompatibility issues from therapy.

Oscillating and variable output of the current over time for various therapeutic reasons.

Protection of all of these specifically to the different pathogens: HIV, Viral Hepatitis, MRSA and antibiotic resistant bacteria, vector borne diseases, fungal, protozoa and prions On skived electrode design, must protect the extended tip with a domed end, this is a critical design invention that allows a safer, more comfortable insertion placement of our electrode. Extended insulation beyond last skived/open window that exposes the metal must be at minimum 0.5" and have a domed end AND cover also a blunt end where the actual tip, blunt end of the wire can be seen (i.e. As if you cut a piece of electrical wire and looked at the end, seeing the interior wire encompassed by the insulating material) with same specifications of how much must be inserted into patient As used herein, the term "patient" refers not only to a human, but also to mammals and even animals in general; the terms "rod" or "wire" refer to a thin, straight, and rigid or flexible bar; the term "aleated" means completely coated or insulated except for a small portion.

In a particular embodiment, the current invention is a device for treating an infection within a patient's bloodstream comprising an iontophoretic wire, where the iontophoretic wire comprises one or more metals which have a proven ability to give off ions effective in killing pathogens, including but not limited to silver, gold and copper.

In another embodiment, the current invention is a method for killing a pathogens (virus is just one form of blood borne pathogen: pathogens bacteria, viral, fungal, parasites and prions) within a patient comprising the steps of inserting the device into the blood supply of the patient and allowing the patient's blood to flow around an iontophoretic wire.

There has thus been outlined, rather broadly, the more important features of the invention in order that the detailed description thereof may be better understood, and in order that the present contribution to the art may be better appreciated. There are additional features of the invention that will be described hereinafter and which will form the subject matter of the claims appended hereto. The features listed herein and other features, aspects and advantages of the present invention will become better understood with reference to the following description and appended claims.

BRIEF DESCRIPTION OF THE FIGURES

The accompanying drawings, which are incorporated in and form a part of this specification, illustrate embodiments of the invention and together with the description, serve to explain the principles of this invention.

DETAILED DESCRIPTION OF THE INVENTION

Many aspects of the invention can be better understood with the references made to the drawings below. The components in the drawings are not necessarily drawn to scale. Instead, emphasis is placed upon clearly illustrating the components of the present invention. Moreover, like reference numerals designate corresponding parts through the several views in the drawings.

Figure 1:
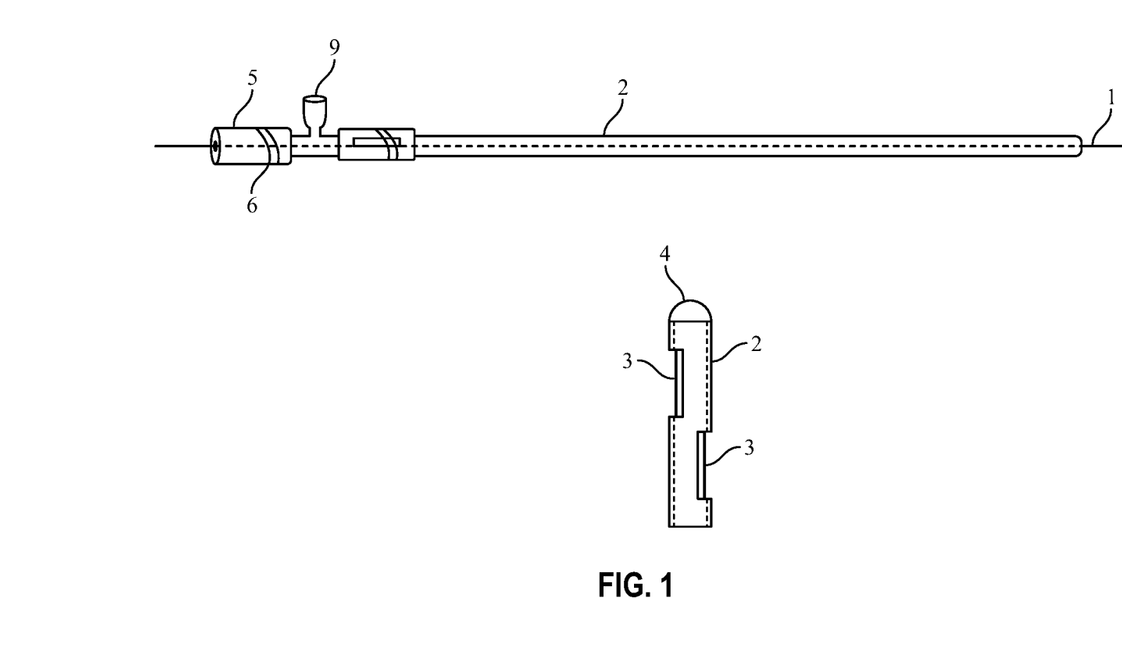
FIG. 1 is a front view of a device and method for killing pathogens in blood of a patient according to selected embodiments of the current disclosure.

FIG. 1 is a front view of a device and method for killing pathogens in blood of a patient according to selected embodiments of the current disclosure. A wire 1 is protected by an insulated covering 2. The wire 1 and insulated covering 2 are inserted into the bloodstream of a patient via a catheter. The actual composition of the wire 1 can be varied depending on the treatment desired. Among the contemplated wires are 100% silver, 100% gold, 100% copper, and various combinations thereof, with preferred embodiments of the invention having anywhere from 70% or more of one the three main metallic options and the remaining 30% from one or a combination of the two remaining materials.

Once the wire 1 is in the patient's bloodstream, the wire 1 releases ions which kill pathogens which reside within the patient's bloodstream that flow around the wire 1. The insulated covering 2 protects both the wire 1 from being damaged, the patient from being injured by the wire 1 breaking off inside the patient's bloodstream and ensures that the proper release of ions for therapy is delivered to destroy the target pathogen(s). At the proximal portion of the invention is a male Luer lock 5 connecting with a female Luer locks 7. The Luer locks protect the more sensitive components and provide threads or other mating items to avow it to be connected to a catheter 11. Within the male lure 5 is a copper pin 6 or other conductive material for the low intensity direct current by which the device is connected to a power supply 50. The purpose of the pin is to supply low intensity direct current to the device which creates the ionic release, or actually accelerates the ionic release. The wire on its own in the blood will release ions, but not at the rate and volume required to effectively destroy pathogens.

FIG. 1 also shows a different embodiment of the same general idea. Rather than having an insulated covering 2 covering all of the wire 1 other than its tip, this embodiment has the insulated covering 2 covering the entire wire 1, with a domed cap 4 completing the protection of the wire 1. This embodiment has one or more cut-outs 3, which expose the wire to the blood stream, and allow the wire to release the desired ions. This second embodiment is more secure than the first, as there is no barren wire 1 within in the blood stream.

The device and method work as follows: The electrode wire is annealed and insulated up to the exposed tip or cut outs so that no ions are released from anywhere other than the intended release point, critical to the therapy, which is well into the vein and flow of blood. This will ensure that there will not be any exposed wire prior to that point there will be ionic release resulting in less than ideal volume of ions released to reach and treat the target pathogen. Due to the rapid release of up to trillions of ions per second, the proximity of the free or bare metal or wire must be a minimum of ½" beyond the tip of the introducer needle or catheter or from the entry point of the vein.

The inventor has found that the volume of ions released from the wire is dependent on the length and/or surface area of exposed metal, such that having the proper exposed wire, either by length or surface area, is directly related to the potential or efficacy for killing the target pathogens. As such, as variety of lengths of exposed wire and variations on how this proper length is exposed is contemplated, as the length and surface areas of exposed wire is critical to the actual ionic release with LIDC (low intensity direct current). The inventor's research has shown that different pathogens require different loads or releases or volumes of ions (similar to different mg doses of a pharmaceutical drug).

The invention contemplates three different application electrodes, each more or less efficient depending on the pathogen targeted. These electrodes include: Central Venous Electrode (CVE); Peripheral Venous Electrode (PVE); and PICC Electrode (PICCE) which is an Electrode placed within a peripherally inserted central catheter or PICC. The length of the annealed or insulated wire extending from the proximal or originating point of the lure is critical to proper placement and delivery of the metallic ions for the treatment of blood-borne pathogens. Therefore, the length of the aleated wire in the different electrode designs is different, but a preferred general embodiment calls for a range from 1.5"-32" long (1.5" to 6" for PVE, 4"-9" for CVE and 15"-32" for PICCE).

The device also relies on waveforms to enhance and increase safety during treatment by this method. The background current waveforms from the device are delivered from the power supply to enhance blood flow to the placement of the electrode and enhance distribution of metallic ions within the venous system to improve the efficacy of the therapy The device provides a range that is from 2.0 billion ions per second to 7.0 trillion ions per second. As time passes the current ranges from 2 billion to 7 trillion ions per second, going up to 7 then slowly down to 2 then slowly back up to 7 and so forth. The variable of how long it takes to ramp up and ramp down the volume of ions released is a variable that can be set from the device controller. This can be a continuous-fixed release below 2 m-7B per second, or this can be variable changing rate anywhere between 2 m-7B.

Figures 2, 3:
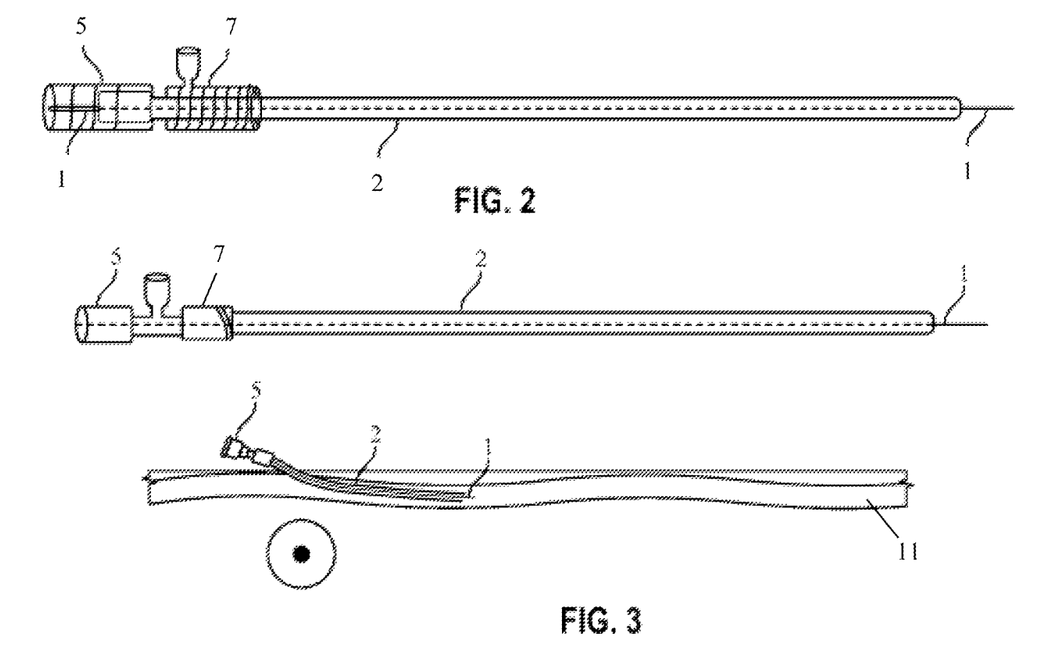
FIG. 2 is another front view of a device and method for killing pathogens in blood of a patient according to selected embodiments of the current disclosure.
FIG. 3 is a front view and a side view of a device and method for killing pathogens in blood of a patient according to selected embodiments of the current disclosure.

FIG. 2 is another front view of a device and method for killing bacteria and viruses in blood of a patient according to selected embodiments of the current disclosure.

Crucial to the success of the device is its use of phased output current. A timed or phased current release allows higher release of metallic ions over certain periods of the treatment, and lower release of metallic ions over the remaining periods of time. One such example is to lower metallic ion release as viral loads are lowered; another is to lower metallic ion release during hours of sleeping, both making the therapy more efficient and comfortable for the patients.

The invention also contemplates a combination catheter that allows for the simultaneous release of silver ions and the administration of an IV antibiotic or other medical therapy via a catheter for the treatment of antibiotic resistant bacteria and other blood borne pathogens or infections. The device ranges from 12-26 gauge to properly introduce electrodes. This range of catheters allows for a range of electrode diameters to be inserted into the blood flow of the patient. This range of catheters allows our range of electrode diameters to avow administration from youth to adults; the connection will allow screw-on or a universal connector to accept the multiple available IV piggyback systems; the external or internal surface of the catheter has a spiral-wound silver wire that is designed for the specific ionic release necessary for the applicable therapy, this varies depending upon the patient's size, age and the type of infection (or infections in multiple symptom patients), therefore, the exposed spiral wire has a range covering a length from 0.5" to 2" of the distal end of this special catheter, with a wide or tight spiral. The spiral is contemplated to be either internal or external. Another embodiment of the idea is to braid the wire into the internal or external surface of the catheter. The distance of the braid from the end of the catheter is contemplated to range from 0.5" to 2.0" from the distal end of the catheter.

The ranges, of spiral or braided wire incorporated into the catheter, specified in this provisional application are the ranges necessary to achieve the proper volume of ionic release in combination with the appropriate volume of antibiotic or other IV medicant for the different infections and patient variables. The basic design of the invention provides that the inserted catheter has a spiral or mesh wound silver wire as part of the catheter make up, allowing it to have the flexibility to be inserted into the venous system; will also have enough metal exposed for the desired volume of metallic ions to be released per second for the therapy; will have a connection point at proximal end of the catheter to connect the low intensity direct current to the catheter so that once the current is turned on it will release the metallic ions for distribution into the venous system; the single or multi lumen catheter will have a connection to an external IV antibiotic or therapy bag so that the desired solution can be administered through a lumen within the catheter and go directly into the venous system.

The combination catheter allows the simultaneous release of metallic ions and the administration of an IV antibiotic or other medicant for the treatment of antibiotic resistant bacteria and other blood-borne pathogens or infections. The gauge of the catheters, used to introduce the metallic electrode devices being described here, ranges from 12-26 gauge to avow administration from youth to adults; the connection will allow screw-on or a universal connector to accept the multiple available IV piggyback systems; the internal surface or external surface of the catheter will have a spiral wound or braided metallic wire (that dimensional range of wire used being 0.001" to 0.020") that will be designed for the specific ionic release necessary for the applicable therapy, this will vary depending upon the patient's size, age and infection, therefore, the exposed spiral wire or braided wire would have a range covering a length from 0.5" to 2" from the distal end of the catheter, with a wide or tight spiral or braid.

The power supply (see, e.g., power supply 50 in FIG. 1) additionally comprises a clamp for input voltage, a regulator to the actual current flowing to the control board (PCB), disallows too much voltage to the circuit board for protection, and a clamp on the output current generator, current regulator, to protect the electrode from receiving too much current as well to protect the ionic release so not too many ions, and to protect the patient from too much current.

The goal is to combine technologies to allow the device to be used on a greater range of pathogens, the ranges of items mentioned allows a user of the invention to custom-tailor the iontophoretic release of metallic ions for the target pathogen. This combination also lowers the production cost of the electrode thus making the therapy more affordable; providing a "wider therapeutic window" for treatment; make the placement of the electrode safer and more comfortable to the patients; makes the application of device "less invasive".

FIG. 3 is a front view and a side view of a device and method for pathogens within blood of a patient according to selected embodiments of the current disclosure. This figure shows how the length of the wire 1 that is exposed, that is not covered by insulated covering 2, can vary. A preferred embodiment is 0.1" to 1.00".

As can be seen in this illustration, the introduction of metal ions via insertion of a wire into the venous system of a patient is superior to the prior art of IV drip and iontophoretic release through skin applied pads, as these methods do not produce enough ions and also does not get the ions into the venous system in high enough volumes to be effective in denaturing or destroying the target blood-borne pathogens. Therefore, to effectively treat the target pathogens it is required to have the production of a medicant directly within the venous system in excess of 2 billion ions per second.

Research by the inventor has shown, especially with certain pathogens, that the time required for treatment may exceed 1-2 days, and that having the ionic release in the chest area can be superior and faster for these extended therapies. To facilitate this method of treatment, the device relies on an electrode that can be used with a peripherally inserted central catheter (PICC). The use of a PICC requires the administrator to measure the proper length required for the patient and to cut it to length before placement, thus the electrode will also need to be modified.

The inventor has discovered that in that the actual "per second" volume of ions released is critical to the success of the therapy. Metallic ions, such as but not limited to silver, gold and copper, have a short life within the body and the venous system. After a short period of time they lose their charge and are filtered and excreted from the body. As well, it is imperative that a certain level of concentration of metallic ions be achieved to have the most efficacy for treating the different pathogens targeted; therefore, the iontophoretic constant release of metallic one, directly in the bloodstream from the range of 2 billion to 7 trillion ions per second.

Research has also determined that with a range of wire diameters, exposed wire of various lengths, annealed wire and volume of ions required that to achieve the appropriate iontophoretic release of metallic cations with the variables stated, an output current from the device in the range of 1.25 to 6.0 micro amps of current for the proper volume release of ions directly within the blood stream for the treatment of blood borne pathogens.

Figure 4:
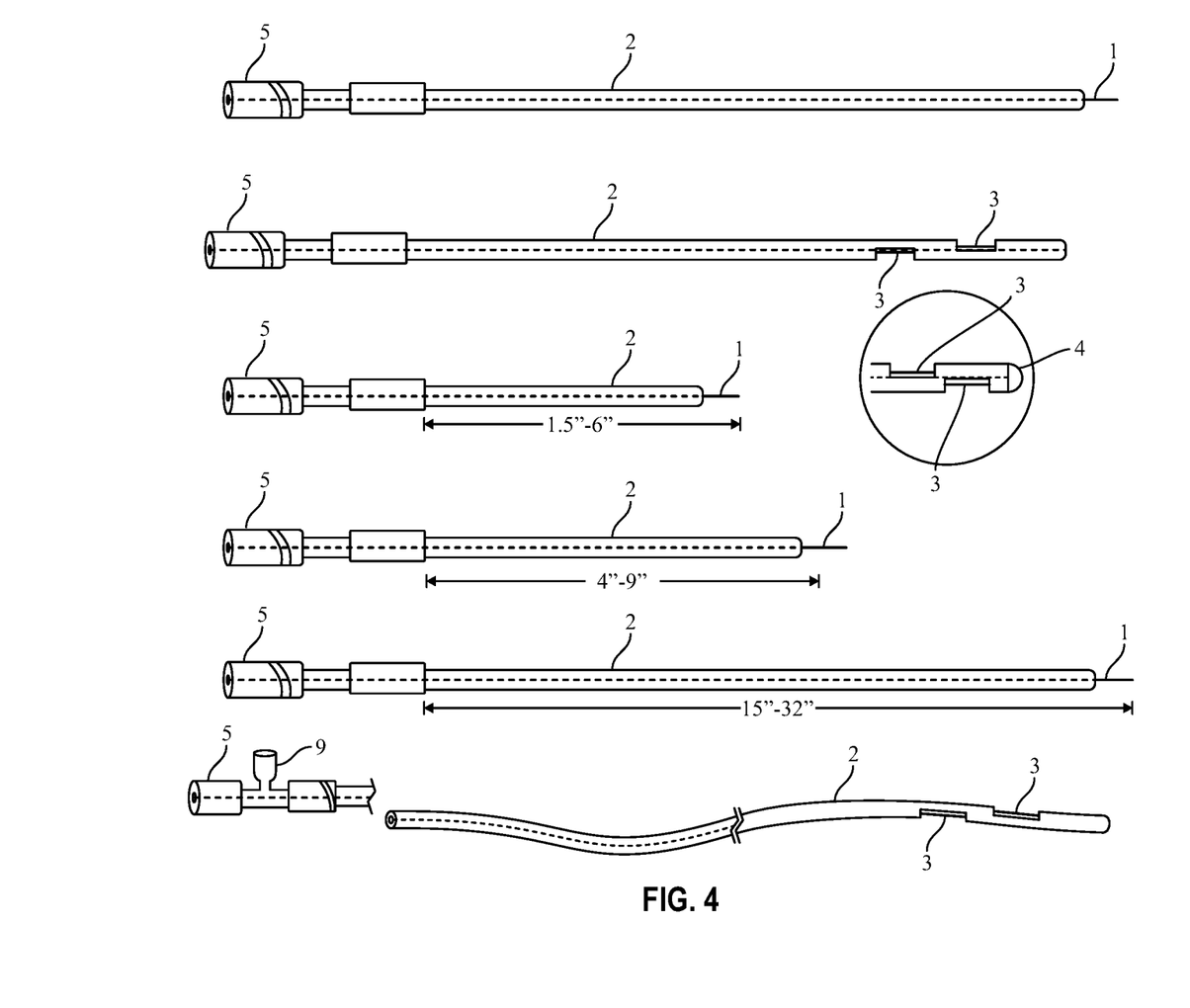
FIG. 4 is a series of front views of a device and method for killing pathogens in blood of a patient according to selected embodiments of the current disclosure.

FIG. 4 is a series of front views of a device and method for pathogens in blood of a patient according to selected embodiments of the current disclosure. This figure shows how the length of both the wire 1 and the insulating covering 2 can be varied. This figure also shows that when the wire 1 has been completely covered by the insulating covering 2 and the domed cap 4 other than for one or more cut-outs 3, the length of exposed wire can be relatively equal to the exposed wire when the wire is allowed to trail from the end of the insulated covering 2. This figure also shows a number of variations in the length of the insulating covering 2 and the wire 1 for different end uses.

Figure 5:
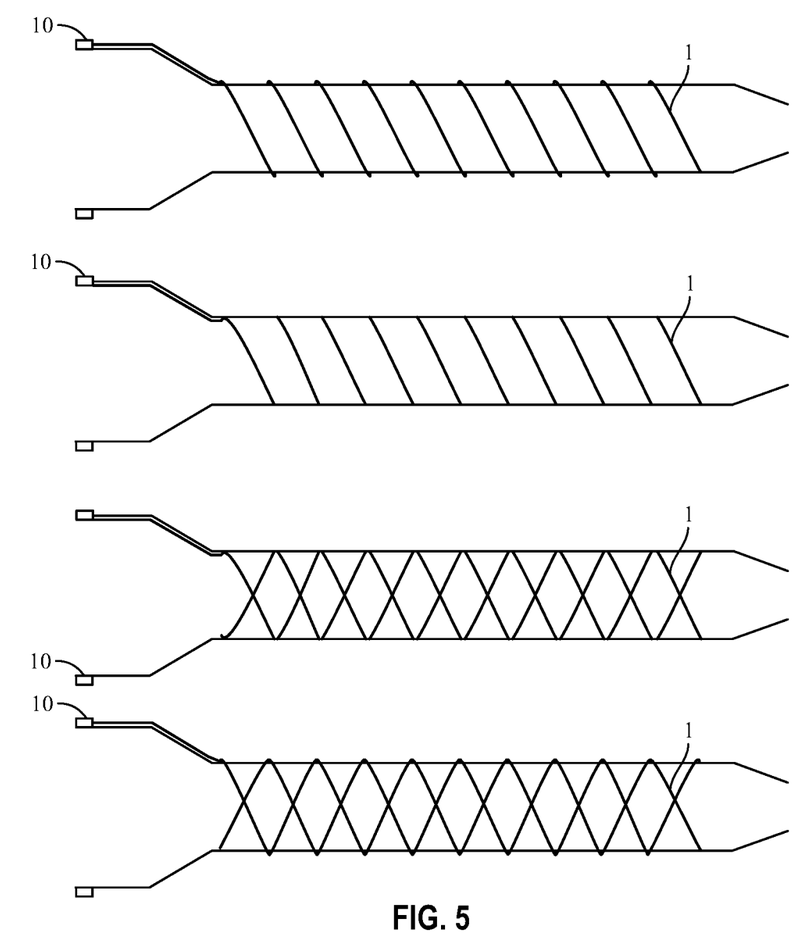
FIG. 5 is a series of front views of a device and method for killing pathogens in blood of a patient according to selected embodiments of the current disclosure.

FIG. 5 is a series of front views of a device and method for killing antibiotic resistant bacteria and pathogens in blood of a patient according to selected embodiments of the current disclosure. FIG. 5 focuses on another embodiment of the idea in which the wire 1, rather than being protected by an insulated covering (2 in other figures) is actually coiled or braided around the catheter 11 and the entire unit inserted into the patient's blood stream. Each end of the wire 1 is connected to a cap connector 10 which is, in turn, connected to the source of power from the power pack (see #8 above) controlling the energization of the wire 1.

Figure 6:
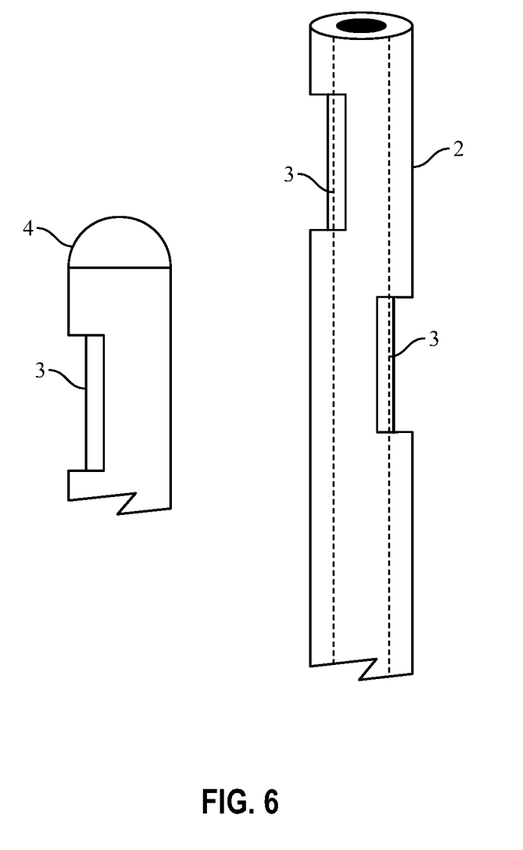
FIG. 6 is a series of front, perspective views of a device and method for killing pathogens in blood of a patient according to selected embodiments of the current disclosure.

FIG. 6 is a series of front, perspective views of a device and method for killing pathogens in blood of a patient according to selected embodiments of the current disclosure. FIG. 6 provides some detailed illustrations of the embodiment of the invention in which the insulated covering 2 covers the entire wire 1, other than for one or more cut-outs 3. The wire 1 is further retained within the insulated covering 2 by a domed cap 4 that seals the open end of the insulated covering 2.

Figure 7:
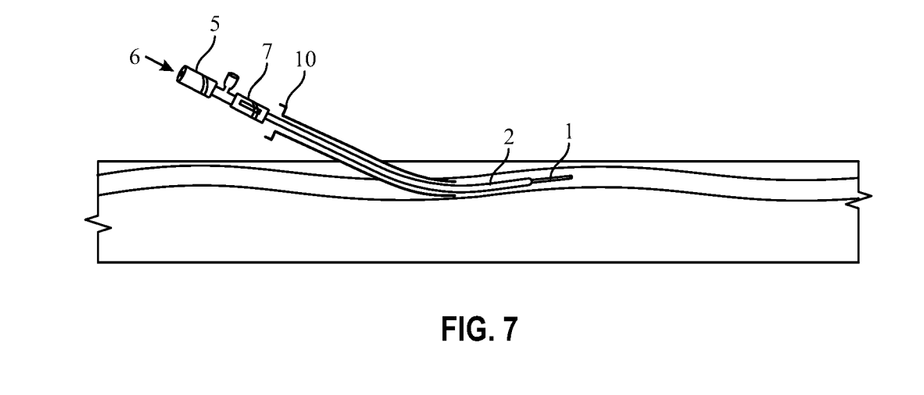
FIG. 7 is a series of front views of the device mounted with a catheter inserted into the vein or artery of a patient.

FIG. 7 is a series of front views of the device mounted with a catheter inserted into the vein or artery of a patient. The wire 1 has been inserted into the vein or artery and is protected by the insulated covering 2. A cap connector 10, male Luer lock 5 and female Luer lock 7 protect a copper (or other appropriate conductive material) pin 6.

Figures 8, 9:
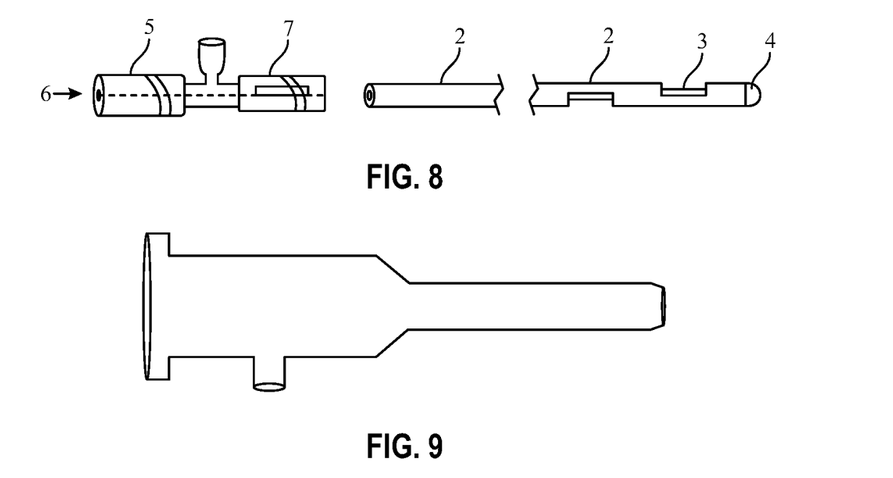
FIG. 8 is a series of front views of a PICCE device.
FIG. 9 is a series of front views of an Open Lumen Catheter for dual therapy. in this figure, an O-ring has been attached to close off around the catheter, which in this case is a specifically design designed catheter.

FIG. 8 is a series of front views of a PICCE device. In this embodiment of the invention, an insulated covering 2 extends all the way to the domed cap 4. One or more cut-outs 3 provide access from the wire to the blood stream.

FIG. 9 is a series of front views of an Open Lumen Catheter for dual therapy. In this figure, an O-ring has been attached to close off around the catheter, which in this case is a specifically designed catheter. There is a port to avow for the administration of IV antibiotics or other desired medications. The inner diameter of the catheter is greater than the outer diameter of the inserted RAIN electrode such that anything added through the port will easily flow into the patient's blood flow.

A particularly preferred embodiment of the invention provides:

A device for treating a blood borne pathogen within a blood stream comprising
an iontophoretic wire (see, e.g., iontophoretic wire 1 of FIG. 1), where the iontophoretic wire comprises one or more metals; a transformer (see, e.g., transformer 20 of FIG. 1), where the transformer comprises a plurality of resistors (see, e.g., plurality of resistors 30 of FIG. 1) and a transducer (see, e.g., transducer 40 of FIG. 1), where the transformer is in electrical connection with the power supply (see, e.g., power supply 50 of FIG. 1), where the one or more metals contains a combination of copper and a second metal,
where the iontophoretic wire additionally comprises an electrode, where the electrode comprises a vein portion and an exterior portion, where the vein portion is inserted into a patient's vein, where the exterior portion is located outside of the patient's vein, where the exterior portion is insulated with an exterior insulation such that no ions are released from anywhere other than an intended release point, where the intended release point is located inside the patient's vein, where the vein portion is at least ½" beyond the tip of an introducer needle and an introducer catheter, where the exterior insulation is an FDA-approved material, where the FDA-approved material is selected from the group consisting of synthetics and plastic material,
where the exterior insulation of the iontophoretic wire has a durometer, where the durometer is flexible enough to placed safely within the patient's venous system without causing an amount of irritation,
where the exterior insulation of the iontophoretic wire has a thickness of between 0.005 and 0.025 inches, where the vein portion has a vein portion length, where the vein portion length is between 0.2 and 1.0 inches,
where the vein portion has a vein portion surface area, and where the vein portion surface area is between 0.005 square inches and 0.70 square inches, where an output current from the device has a range of 1.25 to 6 micro amps of current,
where the production of a medicant directly within a vein of a patient is greater than 2 billion ions per second.

In another embodiment, the electrode is a two-part electrode with a first electrode part and a second electrode part, where the first electrode part is a proximal end unit, where the proximal end contains a conductive pin, where the conductive pin comprises copper, where the conductive pin is held within a Luer lock, where the conductive pin allows the transfer of a low intensity direct current to the iontophoretic wire from the power supply, where the pin can be tightened onto the second part through a tightening device (see, e.g., tightening device 60 of FIG. 1), and where the second part is a second part electrode, where the second part electrode has a length of exposed wire at the distal end.

In alternative embodiments, the length of exposed wire at the distal end is a bare silver wire or a skived window.

In various embodiments, the tightening device (see, e.g., tightening device 60 of FIG. 1) can be a setscrew or a quantity of conductive glue.

It is also contemplated that the metals used can included a wide range of metals, including but not limited to copper, gold and silver, in various combination. This would include embodiments where there are three metals, a first metal, a second metal, and a third metal, and where the first metal is silver, and where the three metals include at least 70% silver and less than 30% of a combination of the second metal and the third metal. Alternatively, the first metal could be gold, and where the three metals include at least 70% gold and less than 30% of a combination of the second metal and the third metal. In yet another embodiment, the electrode comprises at least 70% Copper, or, has between 1% and 99% each of gold, silver and copper.

In various embodiments, the wire can be tempered and/or annealed for proper ionic release and safety of usage of the wire within the venous system.

The device has an output current from the device is in the range of 1.25-6 microamps of current, and, where the production of a medicant directly within the venous system in greater than 2 billion ions per second.

The device can additionally comprise a combination catheter, where the combination catheter allows the simultaneous release of a quantity of metallic ions and a quantity of an IV medicant, such as an IV antibiotic, for the treatment of a quantity of antibiotic resistant bacteria and other bloodborne pathogens, where a gauge of the device will range from 12-26 gauge to avow administration from youth to adults; with an IV connection that allows a universal connector to accept multiple available IV piggy back systems; where an external surface of the catheter comprises a spiral wound silver wire, where the exposed spiral wire has a spiral wound silver wire range comprising a length from 0.5" to 2", and additionally comprising a spiral diameter, where the spiral diameter ranges from 0.001" to 0.1".

Dual Therapy Catheter

A catheter as shown in attached drawing which has a threaded or snap type side port to allow either connection, piggy back, to an IV bag connection or similar readily available medical means of adding an IV antibiotic or other medicant.

Also critical to the design is the fact that the ID of the catheter will be greater than the OD of the utilized RAIN Electrode; having a greater ID will allow any added IV antibiotic or added medicant to flow easily down and around the RAIN electrode and flow into the venous or blood flow of the patient, creating a combination therapy device.

It should be understood that while the preferred embodiments of the invention are described in some detail herein, the present disclosure is made by way of example only and that variations and changes thereto are possible without departing from the subject matter coming within the scope of the invention.

That which is claimed:

1. A device for treating a blood-borne pathogen within a bloodstream, the device comprising:
    an iontophoretic wire, where the iontophoretic wire comprises two or more metals including a combination of copper and a second metal;
    a transformer, where the transformer comprises a plurality of resistors and a transducer, where the transformer is in electrical connection with a power supply,
    where the iontophoretic wire additionally comprises an electrode, where the electrode comprises a vein portion and an exterior portion, where the vein portion is inserted into a patient's vein, where the exterior portion is located outside of the patient's vein, where the exterior portion is insulated with an exterior insulation such that no ions are released from anywhere other than an intended release point, where the intended release point is located inside the patient's vein, where the vein portion is at least ½" beyond a tip of an introducer needle and an introducer catheter, where the exterior insulation is a FDA-approved material, where the FDA-approved material is selected from the group consisting of synthetics and plastic material,
    where the exterior insulation insulating the exterior portion of the electrode of the iontophoretic wire has a durometer, where the durometer is flexible enough so that the vein portion of the electrode of the iontophoretic wire is placed safely within a venous system of the patient without causing an amount of irritation, where the exterior insulation of the iontophoretic wire has a thickness of between 0.005 and 0.025 inches, where the vein portion has a vein portion length, where the vein portion length is between 0.2 and 1.0 inches,
    where the exterior insulation insulating the exterior portion of the electrode of the iontophoretic wire has a thickness of between 0.005 and 0.025 inches, where the vein portion has a vein portion length, where the vein portion length is between 0.2 and 1.0 inches,
    where the vein portion has a vein portion surface area, and where the vein portion surface area is between 0.005 square inches and 0.70 square inches, where an output current from the device has a range of 1.25 to 6 microamps of current, where production of a medicant directly within the patient's vein that is generated by the vein portion of the electrode is greater than 2 billion ions per second.

2. The device of claim 1, where the electrode is a two-part electrode with a first electrode part and a second electrode part, where the first electrode part is a proximal end unit, where the proximal end unit contains a conductive pin, where the conductive pin comprises copper, where the conductive pin is held within a Luer lock, where the conductive pin allows transfer of a low intensity direct current to the iontophoretic wire from the power supply, where the pin can be tightened onto the second electrode part through a tightening device, and where the second electrode part has a length of exposed wire at a distal end of the second electrode part.

3. The device of claim 2, where the length of exposed wire at the distal end of the second electrode part is a bare silver wire.

4. The device of claim 2, where the length of exposed wire at the distal end of the second electrode part is a skived window.

5. The device of claim 2, wherein the tightening device is a setscrew.

6. The device of claim 2, wherein the tightening device is a quantity of conductive glue.

7. The device of claim 1, wherein the second metal is a combination of gold and silver.

8. A device for treating a blood-borne pathogen within a bloodstream of a patient, the device comprising:
    an iontophoretic wire, where the iontophoretic wire comprises one or more metals; and
    a transformer, where the transformer comprises a plurality of resistors and a transducer, where the transducer is in electrical contact with a power supply, wherein the iontophoretic wire additionally comprises an electrode, where the electrode is inserted into a vein of the patient, and where the device releases ions of the one or more metals into the bloodstream of the patient.

9. The device of claim 8, where the electrode comprises a vein portion and an exterior portion, where the vein portion is inserted into the patient's vein, where the exterior portion is located outside of the patient's vein, where the exterior portion is insulated with an exterior insulation such that no ions are released from anywhere other than an intended release point, where the intended release point is located inside the patient's vein, where the vein portion is at least ½" beyond a tip of an introducer needle and an introducer catheter, where the exterior insulation is a FDA-approved material, where the FDA-approved material is selected from the group consisting of synthetics and plastic material.

10. The device of claim 9, where the exterior insulation insulating the exterior portion of the electrode of the iontophoretic wire has a durometer, where the durometer is flexible enough so that the vein portion of the electrode of the iontophoretic wire is placed safely within a venous system of the patient without causing an amount of irritation.

11. The device of claim 10, where the exterior insulation insulating the exterior portion of the electrode of the iontophoretic wire has a thickness of between 0.005 and 0.025 inches, where the vein portion has a vein portion length, where the vein portion length is between 0.2 and 1.0 inches.

12. The device of claim 11, where the vein portion has a vein portion surface area, and where the vein portion surface area is between 0.005 square inches and 0.70 square inches.

13. The device of claim 12, where an output current from the device has a range of 1.25 to 6 microamps of current.

14. The device of claim 13, where production of a medicant directly within the patient's vein is greater than 2 billion ions per second.

15. The device of claim 14, wherein the electrode is a two-part electrode with a first electrode part and a second electrode part, where the first electrode part is a proximal end unit and where the second electrode part has a distal end, where the proximal end unit contains a conductive pin, where the conductive pin comprises copper, where the conductive pin is held within a Luer lock, where the conductive pin allows transfer of a low intensity direct current to the iontophoretic wire from the power supply, where the pin can be tightened onto the second electrode part through a tightening device, where the second electrode part has a length of exposed wire at the distal end of the second electrode part.

16. The device of claim 15, where the length of exposed wire at the distal end is a bare silver wire.

17. The device of claim 15, where the length of exposed wire at the distal end is a skived window.

18. The device of claim 15, wherein the tightening device is a setscrew.

19. The device of claim 15, wherein the tightening device is a quantity of conductive glue.

20. The device of claim 15, where the tightening device for tightening the conductive pin comprising copper onto the second electrode part is a setscrew.

21. The device of claim 15, where the tightening device for tightening the conductive pin comprising copper onto the second electrode part is a quantity of conductive glue.

22. The device of claim 14, where the one or more metals comprise silver.

23. The device of claim 14, where the one or more metals comprise gold.

24. The device of claim 14, where the one or more metals comprise copper.

25. The device of claim 14, where a second metal is a combination of gold and silver.

26. The device of claim 14, where the one or more metals contains a combination of copper, and at least a second metal.

27. The device of claim 26, where the electrode comprises at least 70% copper.

28. The device of claim 26, where the electrode comprises gold, silver, and copper.

29. The device of claim 26, where the wire is tempered for proper ionic release and safety of usage within the venous system.

30. The device of claim 26, where the wire is annealed for proper ionic release and safety of usage within the venous system.

31. The device of claim 26, where an IV medicant is an IV antibiotic to which an infectious agent infecting the patient is not resistant.

32. The device of claim 14 where the one or more metals comprise three metals, a first metal that is silver, a second metal, and a third metal, such that the three metals comprise at least 70% of silver and 30% or less of a combination of the second metal and the third metal.

33. The device of claim 14, where the one or more metals comprise three metals, a first metal that is gold, a second metal, and a third metal, such that the three metals comprise at least 70% of gold and 30% or less of a combination of the second metal and the third metal.

* * * * *